US00PP22860P2

(12) United States Plant Patent

Klemm et al.

(10) Patent No.: US PP22,860 P2

(45) Date of Patent: Jul. 17, 2012

(54) POT CARNATION PLANT NAMED 'KLEDP10112'

(50) Latin Name: *Dianthus caryophyllus*
Varietal Denomination: KLEDP10112

(75) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 13/065,508

(22) Filed: Mar. 23, 2011

(51) Int. Cl.
*A01H 5/00* (2006.01)

(52) U.S. Cl. ..... Plt./278

(58) Field of Classification Search ..... Plt./278
See application file for complete search history.

*Primary Examiner* — Annette Para

(74) *Attorney, Agent, or Firm* — Jondle & Associates, P.C.

(57) ABSTRACT

A new variety of Carnation named 'KLEDP10112' particularly characterized by its dark purple red flowers having a black red edge, a compact growth habit, and purple brown flower buds, is disclosed.

1 Drawing Sheet

Genus and species: *Dianthus caryophyllus*.
Variety denomination: 'KLEDP10112'.

BACKGROUND OF THE NEW PLANT

The present invention comprises a new and distinct variety of Carnation, botanically known as *Dianthus caryophyllus*, and hereinafter referred to by the variety name 'KLEDP10112'. The new variety is the result of a cross conducted in June 2006 in Stuttgart, Germany between the proprietary female parent, 'DCP 05 109' (unpatented) and the proprietary male parent, 'DCP 04 017' (unpatented). A single plant selection was subsequently chosen for further evaluation and for asexual propagation.

The new variety was first propagated via vegetative cuttings in June 2007 in Stuttgart, Germany and has been asexually reproduced repeatedly by vegetative cuttings in Stuttgart, Germany for approximately seven to eight generations. 'KLEDP10112' has been found to retain its distinctive characteristics through successive asexual propagations via vegetative cuttings.

'KLEDP10112' has not been made publicly available or sold more than one year prior to the filing date of this application.

SUMMARY OF THE INVENTION

The following are the most outstanding and distinguishing characteristics of this new variety when grown under normal horticultural practices in a glass greenhouse in Stuttgart, Germany.

1. Dark purple red flowers having a black red edge;
2. A compact growth habit; and
3. Purple brown flower buds.

DESCRIPTION OF THE PHOTOGRAPH

This new Carnation plant is illustrated by the accompanying photograph which shows a close-up of a mature flower and foliage. The colors shown are as true as can be reasonably obtained by conventional photographic procedures. The photograph was taken in April 2010 of a 5-month old plant grown from rooted cuttings in a 10 centimeter pot in a glass greenhouse in Stuttgart, Germany under normal horticultural practices.

DESCRIPTION OF THE NEW VARIETY

The following detailed descriptions set forth the distinctive characteristics of 'KLEDP10112'. The data which define these characteristics were collected from asexual reproductions carried out in Stuttgart, Germany. The plant history was taken in Spring 2010 on 5-month old plants grown in 10 centimeter pots with a minimum pinch date of 45 weeks. The plants were grown in a greenhouse covered with glass. The color readings were determined under natural light. Color references are to The R.H.S. Colour Chart of The Royal Horticultural Society of London (R.H.S.), Fifth Edition (2007).

DETAILED BOTANICAL DESCRIPTION OF THE NEW PLANT

Classification:
- *Family*.—Caryophyllaceae.
- *Genus and species*.—*Dianthus caryophyllus*.
- *Common name*.—Carnation.

Parentage:
- *Female parent*.—The proprietary Carnation 'DCP 05 109' (unpatented).
- *Male parent*.—The proprietary Carnation 'DCP 04 017' (unpatented).

Plant:
- *Form*.—Potted plant.
- *Habit*.—Upright.
- *Height (from top of soil)*.—16.0 cm to 18.0 cm.
- *Width (spread)*.—12.0 cm.
- *Life cycle*.—Partially perennial.
- *Flowering habit*.—Continuous.
- *Time to produce a finished flowering plant*.—5 months.
- *Propagation type*.—Vegetative cuttings.
- *Time to initiate roots*.—16 to 20 days.
- *Root description*.—White, fine.
- *Temperature tolerances*.—Normal.

Branches:
*Strength*.—Medium-strong.
*Quantity per plant*.—5.
*Color*.—RHS 137C.
*Length*.—12.0 cm to 15.0 cm.
*Diameter*.—0.5 cm to 1.0 cm.
*Internode length*.—0.5 cm to 1.0 cm.
*Texture*.—Smooth.

Leaves:
*Arrangement*.—Opposite.
*Shape*.—Lanceolate.
*Apex*.—Acute.
*Base*.—Obtuse.
*Margin*.—Entire.
*Color*.—Immature leaf (both upper and lower surfaces): RHS 136C. Mature leaf (both upper and lower surfaces): RHS 136C.
*Size*.—Length: 3.0 cm to 6.0 cm. Width: 0.5 cm to 0.8 cm.
*Texture*.—Smooth.
*Venation pattern*.—Palmate.
*Venation color*.—Upper surface: RHS 136C. Lower surface: RHS 137C.
*Petioles*.—Absent.

Flowers:
*Type*.—Small sprays.
*Flowering season*.—Spring to Fall.
*Lastingness of individual flowers on the plant*.—12 to 14 days.
*Size*.—Width: 2.5 cm. Depth: 2.0 cm.
*Shape*.—Round.
*Fragrance*.—Present.
*Number of flowers per plant*.—4 to 7.
*Calyx*.—Form: Cylinder vase. Length: 2.0 cm. Width: 1.2 cm.

Flower buds:
*Color*.—RHS 137C and RHS 176C.
*Shape*.—Elliptic.
*Length*.—0.8 cm to 1.2 cm.
*Diameter*.—0.6 cm to 1.0 cm.

Petals:
*Arrangement*.—Arranged in several whorls.
*Quantity* (*per flower*).—Greater than 30.
*Shape*.—Spoon-shaped.
*Apex*.—Obtuse.
*Base*.—Acute.
*Margin*.—Slightly crenated.
*Size*.—Length: 2.0 cm. Width: 1.5 cm.
*Color*.—When opening: Upper surface: RHS 56A and RHS 59A. Lower surface: RHS 56A. When fully opened: Upper surface: RHS 56A and RHS 59A. Lower surface: RHS 56A.
*Texture* (*both upper and lower surfaces*).—Smooth.

Sepals:
*Arrangement*.—Fused.
*Quantity* (*per flower*).—4 to 5.
*Shape*.—Elliptic.
*Apex*.—Acute.
*Base*.—Obtuse.
*Margin*.—Smooth.
*Size*.—Length: 0.6 cm. Width: 0.5 cm.
*Color*.—Upper surface: RHS N136C. Lower surface: RHS 136C.
*Texture* (*both upper and lower surfaces*).—Smooth.

Peduncle:
*Length*.—5.0 cm to 8.0 cm.
*Diameter*.—0.2 cm to 0.3 cm.
*Texture*.—Smooth.
*Color*.—RHS 137C.

Reproductive organs:
*Pistils*.—Quantity: 1. Stigma color: RHS 65A to RHS 65D. Ovary color: RHS 144C.
*Stamens*.—Quantity: Moderate. Filament: Length: 0.5 cm to 0.8 cm. Color: RHS 65A to RHS 65D. Anther color: RHS 65A. Pollen: Amount: Moderate. Color: RHS 65D.

Fruit and seed set: None observed.

COMPARISON WITH PARENTAL AND COMMERCIAL VARIETIES

'KLEDP10112' differs from the female parent 'DCP 05 109' (unpatented), in that 'KLEDP10112' has purple red flowers with a black red edge and a compact growth habit, while 'DCP 05 109' has purple flowers and a strong growth habit.

'KLEDP10112' differs from the male parent 'DCP 04 017' (unpatented), in that 'KLEDP10112' has purple red flowers with a black red edge and dark green foliage, while 'DCP 04 017' has light pink flowers and medium green foliage.

'KLEDP10112' differs from the commercial variety 'SuperTrouper Burgundy' (unpatented), in that 'KLEDP10112' has purple red flowers with a black red edge, a compact growth habit, and double flowers, while 'SuperTrouper Burgundy' has dark red flowers with dark stripes, a medium growth habit, and semi-double flowers.

We claim:

1. A new and distinct variety of Carnation plant named 'KLEDP10112' as shown and described herein.

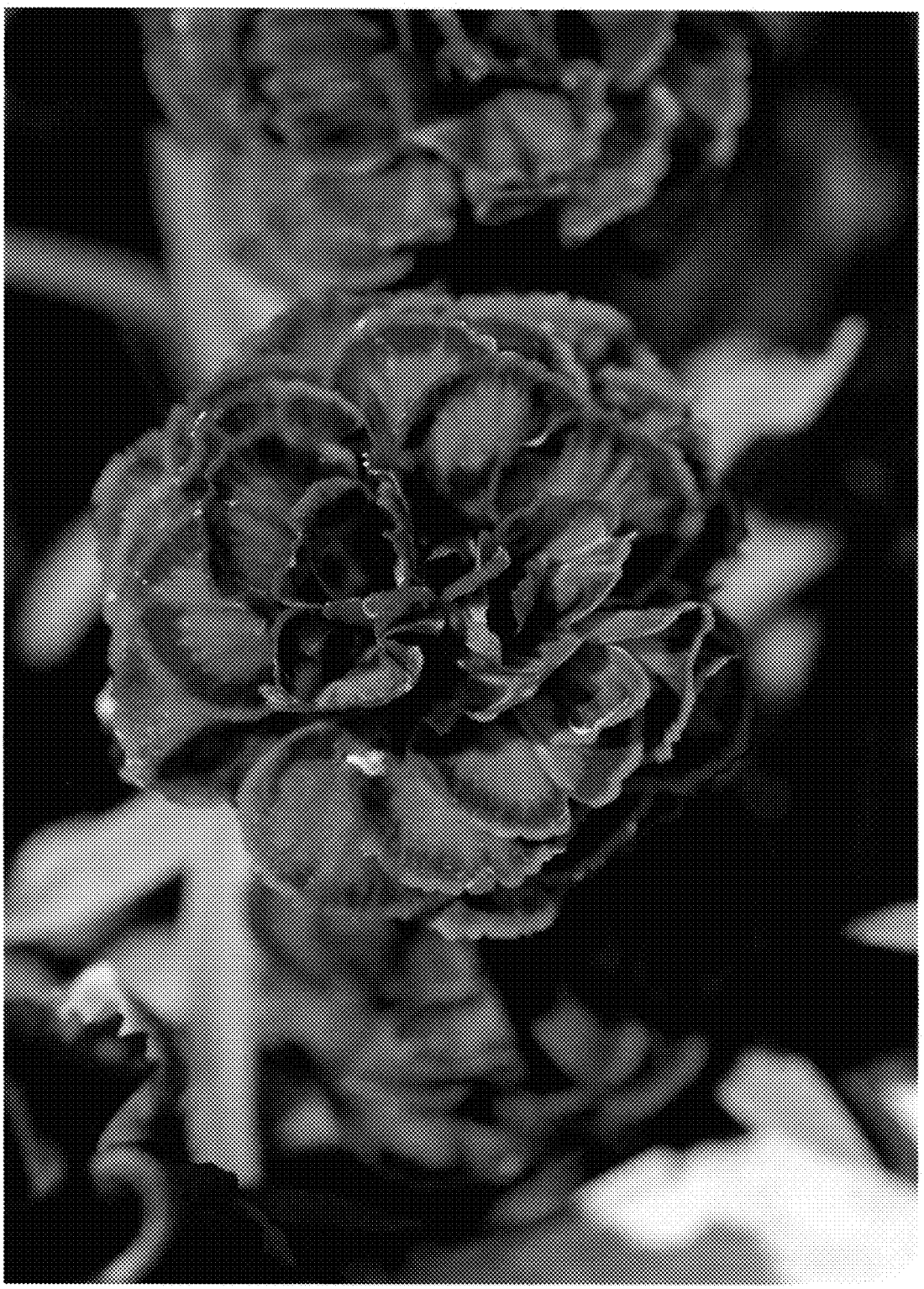

* * * * *